(12) United States Patent
McLennan (10) Patent No.: US 11,159,901 B1
(45) Date of Patent: Oct. 26, 2021

(54) TINNITUS TREATMENT USING SINE WAVE CLUSTERS

(71) Applicant: Thomas Kendall McLennan, Rocklin, CA (US)

(72) Inventor: Thomas Kendall McLennan, Rocklin, CA (US)

( * ) Notice: Subject to any disclaimer, the term of this patent is extended or adjusted under 35 U.S.C. 154(b) by 0 days.

(21) Appl. No.: 17/202,684

(22) Filed: Mar. 16, 2021

Related U.S. Application Data (60) Provisional application No. 63/053,873, filed on Jul. 20, 2020.

(51) Int. Cl.
| | |
|---|---|
| *A61B 8/00* | (2006.01) |
| *H04R 29/00* | (2006.01) |
| *A61M 21/02* | (2006.01) |
| *H04R 25/00* | (2006.01) |
| *A61B 5/12* | (2006.01) |

(52) U.S. Cl.
CPC ............. *H04R 25/75* (2013.01); *A61B 5/128* (2013.01)

(58) Field of Classification Search
CPC .................... A61B 5/128; A61F 11/00; A61M 2021/0027; A61N 1/36036; A61N 1/361; H04R 25/75
See application file for complete search history.

(56) References Cited

U.S. PATENT DOCUMENTS

2004/0141624 A1\* 7/2004 Davis ..................... A61B 5/121
381/73.1
2014/0275737 A1\* 9/2014 Shore ..................... H04R 25/75
600/26

\* cited by examiner

*Primary Examiner* — Christine H Matthews
*Assistant Examiner* — Joshua Daryl D Lannu
(74) *Attorney, Agent, or Firm* — Adam Warwick Bell; Matthew Rupert Kaser (57) ABSTRACT

A highly effective method for treating refractile tinnitus by repeatedly subjecting a subject having tinnitus to a specific calculated sound comprising a group of related waveforms.

18 Claims, 6 Drawing Sheets

Sine

Square

Ramp

Sawtooth

Triangular

FIG. 4

Dead Ringer Effectiveness Survey
*Required

Email address*

Your email

Use this scale to answer the questions below:

- 0 is silence
- 1 is barely there
- 2 is like a fan in the corner on low
- 3 is like the fan on high
- 4 is like the hum of a fluorescent lights while you're having a conversation
- 5 is noticing it while you're trying to talk/listen/focus
- 6 is you being irritated by it as you're trying to talk/listen/focus
- 7 is being to distract you as you try to maintain your train to thought
- 8 is when has your full attention and it's just there in your face
- 9 is it's so loud that it's really starting to hurt
- 10 is the loudest and most unbearable you've ever heard What is the level of your tinnitus before using your treatment track?

1  2  3  4  5  6  7  8  9  10
○  ○  ○  ○  ○  ○  ○  ○  ○  ○

Request edit access

What is the level of your tinnitus immediately after listening to your treatment track?

1    2    3    4    5    6    7    8    9    10

○    ○    ○    ○    ○    ○    ○    ○    ○    ○

What is the level of your tinnitus 1 hour after listening to your treatment track?

1    2    3    4    5    6    7    8    9    10

○    ○    ○    ○    ○    ○    ○    ○    ○    ○

What is the level of your tinnitus 2 hour after listening to your treatment track?

1    2    3    4    5    6    7    8    9    10

○    ○    ○    ○    ○    ○    ○    ○    ○    ○

Any comments, observations, or requests?

Your answer

⬤▭ Send me a copy of my responses.

Submit

FIG. 5 (Continued)

TINNITUS TREATMENT USING SINE WAVE CLUSTERS

RELATIONSHIP TO OTHER APPLICATIONS

This application claims priority to and the benefit of U.S. 63/053,873 titled 'Dead Ringer: A Tinnitus Treatment' and filed 20 Jul. 2020, hereby incorporated by reference for all purposes.

FILED OF THE INVENTION

The field of the invention is the effective treatment for tinnitus, particularly tinnitus that has been refractile to previous treatments.

BACKGROUND

Tinnitus is a pathological condition characterized by the perception of a ringing sound when no external sound is present. It has proved very difficult to treat, despite many years of suffering by hundreds of millions of patients. The present invention provides a clinically proven and highly effective method for treating tinnitus.

Causes of tinnitus may include noise-induced hearing loss, ear infections, inflammation, foreign objects in the ear, nasal allergies, exposure to loud sounds, neurological damage etc. Tinnitus consists of anything from a weak tone up to a continuously audible loud noise, hissing, buzzing or even a very loud tone which is never interrupted. Known manifestations include clicking, rushing or humming, heartbeat, low-pitched ringing and high-pitched ringing.

The incidence of tinnitus for people aged 65 to 84 years is approximately 27 percent. While static or ambient sounds of varying frequencies may be present, the majority of this population experience tinnitus primarily as a pure tone with qualities similar to a sine wave.

Nerve centers between the organ of Corti and the brain are responsible for complex signal processing and perturbations in this system are thought to be responsible for the pathology f tinnitus. When inappropriately stimulated, a sound is perceived by the brain. This sound may be a specific phoneme or tone of a specific frequency. The subject hears the specific tone because the nerve which would normally transmit that audible tone to the brain is continuously stimulated.

Treatments include noise suppression and medications.

Medications include Tricyclic antidepressants, such as amitriptyline and nortriptyline and Alprazolam. But these have side effects and are frequently not helpful.

Noise suppression treatments include: (a) White noise machines, which produce simulated environmental sounds such as falling rain or ocean waves. (b) Hearing aids, which can be especially helpful if you have hearing problems as well as tinnitus. (c) Tinnitus retraining, in which a programmed tonal music is supplied to mask the specific frequencies of the tinnitus, thereby helping you not to focus on the tinnitus sounds. (d) Masking devices which produce a continuous, low-level white noise that suppresses tinnitus symptoms.

Efforts to suppress tinnitus for a certain time have been provided by exposing a subject to various sounds and/or tones of different kinds. These so-called "tinnitus masker" treatments comprise an instrument worn on the head like headphones, which generates sinusoidal tones, narrow-band noise, broad-band noise or white noise. However such treatments have proved to have only marginal beneficial effect. Additionally they are time-consuming, very expensive because they involve clinician time, and involve considerable time and difficulty for the patient. In other cases, a standard hearing aid has been found useful, since the hearing aid boosts the overall background noise level and thus allows the patient to distinguish this from his tinnitus.

The physiology of tinnitus is well investigated. Neurons in the brain are held in check by the principles of their action potential. Neurons hold a negative electrical charge so that positively charged signals from neighboring neurons do not cause them to fire by proximity. Neurons must be exposed to a charge strong enough to break this negative threshold in order to fire a positive charge themselves, as illustrated below.

To illustrate the purpose of this concept, consider a widespread failure of this mechanism. The result is likelihood of neurons that are not part of an intended signal pathway to fire. If enough of these malfunctioning neurons exist, the result is a seizure disorder: a recurring possibility of unintended mass-neuron firing like an electrical storm. When a neuron is part of a naturally intended circuit, it is triggered not by the surrounding electrical potentials, but by neurotransmitters binding to a receptive area called a dendrite. The brain is considered a chemical-electric system because the standard protocol for signal transfer looks something like: Transmitters (chemical molecules) from the point of signal origin's "bottom" (presynaptic dendritic vesicles) bind to the "top" (postsynaptic membrane) of the first receptor in what can be pictured, for engineering purposes, as a linked list. The pattern of molecular neurotransmitters bound to the "top" of a neuron engage in a Na−/K+ exchange, exciting the neuron enough to send an encoded electrical signal down its tail (axon) until it reaches its own supply of neurotransmitters at its own "bottom". The encoded electrical signal causes the release of the chemical equivalent of said encoded signal in the form of neurotransmitters to bind to the top of the next neuron in a linked list, and so on.

Applying this physiological mechanism to tinnitus, the primary auditory cortex is tonotopically organized, which means that neighboring cells in the cortex respond to neighboring frequencies. Tonotopic mapping is preserved throughout most of the audition circuit. The primary auditory cortex receives direct input from the medial geniculate nucleus of the thalamus and thus is thought to identify the fundamental elements of music, such as pitch and loudness. To summarize, clusters of neurons are associated with specific frequencies. The more neurons of the same pitch-dedication firing at once, the louder the perceived tone.

The inventor, whose father suffers from tinnitus, has conducted extensive research into the causes and potential treatments of tinnitus. The inventor has discovered that when exposed to a pure sine wave tone of a frequency close enough in pitch the tinnitus tone of the sufferer (in this case, 12250 hz) the sufferer experiences anywhere between 90-100% reduction of his tinnitus. After ending the exposure, his tinnitus slowly climbs back to its original level over a period of 10 min to 2 hrs positively proportional to time exposed to the tone. This initial work led to the development of the present invention.

One of the key competitor treatments for the present invention "Dear Ringer") is the so-called Neuromonics acoustic desensitization procedure which involves extensive counseling and acoustic therapy. Neuromonics and Dead Ringer both find an approximation of a tone the patient is experiencing. Neuromonics requires the patient to pay an entry fee of about $5,500 and come into a clinic for treatment using more simplistic tone therapy and keep on coming back. Dead Ringer allows the patient to make a one-time purchase with hardware right out of the box. The hardware pairs with a smartphone app. Treatment may be largely self-administered, or may be provided with the participation of a clinician, either in-person or remotely.

Clearly there is a need for methods and devices which comprise a simple, effective treatment for tinnitus. Treatments should be easily accessible and inexpensive compared to the current treatments. They should ideally require considerably less clinician time compared to the current treatments, and should generally be capable of self-administration and automation to a large extent.

The present invention provides such methods and devices.

A number of publications are cited herein and incorporated by reference. These include the following:

U.S. Pat. No. 8,579,796, which discloses a method of treatment of tinnitus wherein an acoustic signal to is provided to a subject, wherein said acoustic signal comprises a non-sinusoidal pulsating electric waveform having a pulse repetition rate less than 100 Hz, and wherein said pulsating electric waveform is selected from the group consisting of square waves, triangle waves, and sawtooth waves, said pulsating waveform further comprises a sequence of three of said waves each of a predetermined duration, and said sequence comprises a first square wave, followed by a triangular wave, followed by a second square wave.

J Neurosci. 2015 Jun. 3; 35(22):8579-92 "Inhibition shapes acoustic responsiveness in spherical bushy cells" Christian Keine et al. This publication particularly discloses repetitive stimulations (100 ms duration, 5 ms cos 2 ramps, 300 ms interstimulus interval, 200-300 repetitions) with stimulation loudness was 20-30 dB SPLs above the respective threshold."

Cognitive neuroscience and neuropsychology. Vol 13 No 4 25 Mar. 2002. "Lateral inhibition in the auditory cortex: An EEG index of tinnitus?" Alexander Kadner et al., This publication discloses that tinnitus related activity changes the intensity dependence of the N100 in a frequency specific manner. The experimental data show statistically significant reductions in the intensity dependence of the N100 in response to 2000 Hz tones and a non-significant increase in the intensity dependence of responses to the tinnitus frequency tones (4000 Hz tones)."

The following publications are also incorporated by reference. The following relate to tinnitus treatment: US20100042024. The following relate to headphones and similar devices: US20140016795; US20100110368; WO2018219094; US20090208042; US20080310666; WO2019177782; US20180324515; EP3393137 and U.S. Ser. No. 09/936,301.

BRIEF DESCRIPTION OF THE INVENTION

In a general embodiment, the invention encompasses a method for treating tinnitus comprising subjecting a subject having tinnitus to a repeated number of sounds starting with a tone at about 9397 Hz followed by successive tones repeated until an approximate match is found with the tone perceived by the tinnitus sufferer. Once the personalized tinnitus tone has been found, the software generates "sine clusters" described below, which are then reproduced by a sound generator and played to the subject on a set clinical schedule, thereby effecting an improvement or reduction in tinnitus symptoms.

One of the most important aspects of the present application, and the impetus to commercialize the Dead Ringer system, is that upon clinical experimentation, the inventor has repeatedly demonstrated UNEXPECTEDLY SUPERIOR RESULTS, as follows: In addition to the consistent 50-100% reduction results I have achieved with my father, Case Study Owen Amman has used a 1-hour ACR cluster track designed by Derek Holley roughly 3 times per week for the last 6 weeks, and it has taken his tinnitus from a 4 to a 0 each time for several hours following each instance: a 100% reduction.

DETAILED DESCRIPTION OF THE INVENTION

General Disclosures and Definitions

This specification incorporates by reference all documents referred to herein and all documents filed concurrently with this specification or filed previously in connection with this application, including but not limited to such documents which are open to public inspection with this specification. All numerical quantities mentioned herein include quantities that may be plus or minus 20% of the stated amount in every case, including where percentages are mentioned. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example, "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). When, in this specification, a range is given as "(a first number) to (a second number)" or "(a first number)-(a second number)", this means a range whose lower limit is the first number and whose upper limit is the second number. For example, "from 40 to 70 units" or "40-70 units" means a range whose lower limit is 40 units, and whose upper limit is 70 units.

Wavelength (λ): the wavelength is the spatial period of a periodic wave—the distance over which the wave's shape repeats. It is the distance between consecutive corresponding points of the same phase on the wave, such as two adjacent crests, troughs, or zero crossings. Wavelength is inversely proportional to frequency of the wave: waves with higher frequencies have shorter wavelengths, and lower frequencies have longer wavelengths.

Spatial frequency: this is the inverse of the wavelength.

Tinnitus: is a pathology characterized by the perception of a sound, often a continuous tone, when no external sound is present.

Subject: As used herein the term "subject" means any human person subjected to the treatment described herein.

Clinician: As used herein the term "clinician" means a person administering the treatment described herein, and does not imply any particular degree of medical training.

Sine cluster: as used herein a "sine cluster" refers to a group of three or more sine waves of similar amplitude but varying frequency comprising at least a base frequency sine wave, a sine wave with a frequency n % above the base frequency, and a sine wave with a frequency n % below the base frequency. Other frequencies evenly spaced apart from the base frequency may additionally be included. Rather than indicate a percentage difference, we may also refer to a difference in frequency of a certain number of degrees. Note that in other embodiments, the waveforms may not be sine waves, but may be square-shaped, saw-shaped etc. So when we refer to a sine-wave cluster it is implied that we may also be describing waves having other shapes. In use, the amplitudes may vary up to whatever level the audio technician decides, but amplitude is generally not varied significantly.

Personalized tinnitus tone refers to a tone identical to or approximating to the tone perceived by the tinnitus sufferer.

Additionally, the inventor has categorized perceived tinnitus sounds in the form of a "noise catalog". The inventor has separated tinnitus into two categories: simple and complex. The simple "pure tone" is can be represented with a single waveform and targeted with clustered transformations of that wave. The complex form is the type of tinnitus that people describe as "buzz/fuss" or a "dull roaring", and is comprised of different pitches at varying volumes. The same principle that applies to the simple cases can also be applied to the more complex cases, i.e. recreating a physical representation of what the patient is hearing and presenting that sound to their brain should invoke the same internal dampening of that noise. To this end the inventor is creating an objective catalog of sounds that can be used to define a vocabulary: when we say "buzzing," this is the type of noise we mean, and when we say "roaring," this is the type of noise we mean. The method of the invention can therefore be adjusted to provide to the patient a plurality of Sine Clusters, each comprised of a group of three or more sine waves of similar amplitude but varying frequency. Each sine cluster will be bases on a root frequency. The quality and tone of the sounds may be adjusted to approximate to each of the individual sounds comprising the complex tinnitus sound experienced.

The Invention

The invention encompasses a treatment that reduces perceived tinnitus by 50-100%.

In a general embodiment, the invention encompasses a method for treating tinnitus comprising the steps of subjecting a subject having tinnitus to a repeated number of sounds, starting with a tone at about 9397 Hz followed by successive tones repeated until an approximate match is found with the tone perceived by the tinnitus sufferer. Once the personalized tinnitus tone has been found, the software generates "sine clusters" described below, which are then stored and reproduced by a sound generator, and played to the subject on a set clinical schedule, thereby effecting an improvement or reduction in tinnitus symptoms.

The design of the hardware of the invention allows for the patient to use a discrete, on-the-go headband utilizing bone conduction. Other embodiments use SoundBeamer technology from Noveto Systems, which uses a 3-D sensing module and locates and tracks the ear position sending audio via ultrasonic waves to create sound pockets by the user's ears. Sound can be heard in stereo or a spatial 3-D mode that creates 360 degree sound around the listener. This technology is encompassed in U.S. Ser. No. 14/443,019 which is hereby incorporated by reference.

As stated above, one of the key competitor treatments for the present invention "Dead Ringer") is the so-called Neuromonics acoustic desensitization procedure which involves extensive counseling and acoustic therapy. Neuromonics and Dead Ringer both find an approximation of a tone the patient is experiencing. Neuromonics requires the patient to pay an entry fee of about $5,500 and come into a clinic for treatment using more simplistic tone therapy and keep on coming back. Dead Ringer allows the patient to make a one-time purchase with hardware right out of the box. The hardware pairs with a smartphone app. Treatment may be largely self-administered, or may be provided with the participation of a clinician, either in-person or remotely.

Unlike Neuromonics acoustic desensitization procedure which involves extensive counseling and acoustic therapy and uses a single pure tone sine wave, the present invention uses "sine clusters." Because the auditory cortex is localized (e.g. the neurons responsible for 8,000 hz will be right next to the neurons responsible for 8,010 hz), the present invention provides a sound file that, for the first 15-30 minutes plays back the patient's unique tinnitus tone coupled with a sine wave approximately 0.5% higher and 0.5% lower in frequency than the primary tone. The rationale behind using these sine clusters is that activating as much of the neural auditory pathway as possible will release its inhibitory, counterbalancing neurotransmitters (GAB Aa and GABAb).

The invention relates only to tinnitus which is perceived as a tone. In these cases, it is normally possible to identify a specific, often narrow frequency range within which the tinnitus frequency is located. If, on the other hand, a tone generator repeatedly and slowly moves through this frequency range, then it may be expected that the true tinnitus frequency is actually and repeatedly produced, although the patient does not exactly know when this is the case.

The task of the invention is thus to create a tinnitus masker of the type mentioned at the start, which appears to be particularly suitable, on the basis of tests, for treatment of the kind of tinnitus mentioned above, which makes itself noticeable by supposed hearing of a tone or tone mixture located in the audio frequency range.

Hypothesis

The currently accepted hypothesis is weakly supported and states that tinnitus simply occurs due to ambient electrical activity causing certain auditory neurons to fire consistently enough to create a "phantom" tone. This belief effectively states that with old age, certain neurons in the auditory cortex lose their neural plasticity (i.e. their ability to adapt) and begin to dysfunction via ambient electricity, causing them to erroneously fire.

The inventor's hypothesis disagrees that it is simply ambient charges causing these action potentials. He suggests that clusters of related frequency-dependent neurons engage in a loop of seizure-like activity, cycling around and around to activate and reactivate their neighbors after exposure to the initial ambient "noise". The brain is a chemical-electric system, so if the cause is primarily electrical in nature, the chemicals that are supposed to modulate and inhibit these neurons are not being released. I assert that when the whole auditory pathway is stimulated via exposure to an identical "real" (physical) frequency, the modulating chemicals are finally released, thereby heavily dampening the cyclical "sound seizure". When exposure to this tone ends, my educated guess is that these chemicals slowly stop being released, hence the gradual return of the tinnitus.

Further, my own case-study (single patient) research has suggested that the frequency of the tinnitus tone may change or simply stop responding to a single identical tone. For this reason, my approach involves the use of two key methods.

Based on the current leading hypothesis re: hearing loss and longevity, the inventor reasons that due to the recursive structure of balancing-to-equilibrium found throughout the brain within the continuing research in regards to neuroplasticity, pitches are somehow "cancelled" in order to reset/prepare for more input faster than would be the natural rate of signal decay. Population testing shows a deterioration of lower-mid pitch audition, which implies that a range of lower pitches is being received (in cases of absent or insignificant sensory pathway physiology), but these signals are not being carried at a correctly "loud" level of intensity throughout the Auditory Cortex. The situation described could explain the high-pitched ringing reported by sufferers of tinnitus. This explanation will allow for treatment via "correct" physically received auditory signaling through design. The present invention provides such a design by first providing a pitch-match of an approximate frequency perceived by a tinnitus sufferer using a computer-generated sine wave. A high-low iterative process allows more accurate approximation rather than attempting to adjust in real-time due to the likely confusion of sensation.

Device Concept

The inventor suggests that a device resembling the daily usage of hearing aids (removable, but with intended all-day use) can be used with the current invention to treat tinnitus. This provides the advantage of low production cost and high availability. This device has two primary components: the ear buds and a controller module. Most ear buds on the market attempt to block the entire ear canal, but I the inventor reasons that with the earpiece could include a large notch so that the wearer would have no problem hearing the world around them while their personalized tinnitus tone discreetly plays into their ears. This ear bud would need to be able to play pure sine waves covering the entire human hearing range (40 hz-20 khz) within a 2-5% accuracy margin to a specific frequency. The controller module is adapted to plug into this earpiece and, on first use, help the patient find their symptom's wave frequency using a "binary chop" algorithm: The patient begins with a tone generated at 9397.272573 hz (a D9 in music theory) for 3-10 seconds, decides if their tinnitus is higher or lower, and presses either "Higher", "Lower".

The controller jumps up or down by an octave. The patient is then prompted with "Higher" or "Lower" again with a new option of "This is in the ballpark range of my tinnitus". When the patient selects "This is in the ballpark range of my tinnitus", the algorithm stops jumping up and down by octaves. It the prompts the user with a tone that they can respond "Higher" or "Lower" to, but will be jump up and down by the 7 notes in the octave of a key signature. The key signatures we will use as the algorithm develops are: C Major, G major, E flat Major, D Major, A Major, E Major, D flat major, B flat Major, A flat Major, B major, and F sharp Major. Once the patient has honed in closer to the note, the algorithm will break out of key signatures and use half-steps on the chromatic scale. "Higher" and "Lower" will then increment up and down in the same way one might envision using the white and black keys on a piano.

Once the chromatic higher/lower process has honed even closer to the patient's tinnitus tone, the algorithm will switch to something more like a fine-tuning knob on a guitar or violin. Once the patient is satisfied with their approximation, the software will save the frequency Hz value as their "personalized tinnitus tone."

Once that personalized tinnitus tone has been found, the software will generate so-called "sine clusters".

A sine cluster is defined as a group of at least three sine waves of similar amplitude comprising (i) a base frequency which is identical to the personalized tinnitus tone (ii) a sine wave with a frequency n % above the base frequency, and (iii) a sine wave with a frequency n % below the base frequency. The percentage "n" may be any suitable percentage including 0.5%, 1%, 5%, 7%, 10%, 20%, 30% and 40% and any range between these stated percentages, or between 0.5 and 45%. The sine cluster may include any odd number of sine waves intentionally spaced apart relative to the personalized tinnitus tone.

Once the A sine cluster has been established, it is recorded or imprinted or programmed into an audio output device and provided to the subject on a set schedule, over a set period of time, thereby effecting a reduction in tinnitus symptoms.

Embodiment 1—a General Treatment Embodiment

In a general embodiment, the invention encompasses a method for treating tinnitus comprising subjecting a subject having tinnitus to a sound, whereby the following steps are performed:

Providing a subject suffering from tinnitus and

1—providing to the subject a tone between 9000 Hz and 10000 Hz, for between 1 and 10 seconds 2—grading the tone by the subject as either higher or lower in tone than the perceived tinnitus tone 3—adjusting the tone either up or down by one octave 4—grading the tone by the subject as either higher or lower in tone than the perceived tinnitus tone 5—repeating steps 3-4 until an approximate match is found with a resolution of no more than one octave 6—adjusting the tone up or down by 7 notes at a time 7—grading the tone by the subject as either higher or lower in tone than the perceived tinnitus tone 8—repeating steps 6-7 until an approximate match is found with a resolution of no more than 7 notes 9—adjusting the tone up or down by half notes (e.g.: C, C#, D, D#, E, E#)

10—grading the tone by the subject as either higher or lower in tone than the perceived tinnitus tone
11—repeating steps 9-10 until an approximate match is found with a resolution of no more than half a note
12—adjusting the tone up or down on a continuous scale
13—grading the tone by the subject as either higher or lower in tone than the perceived tinnitus tone
14—repeating steps 12-13 until an approximate match is found such that no further adjustments in tone produce a perceived improved match ("personalized tinnitus tone")
15—saving the personalized tinnitus tone information including wavelength, frequency and amplitude, in a computer memory
16—generating by means of computer software, one or a plurality of sine clusters, wherein a sine cluster is defined as a group of three sine waves of similar amplitude but varying frequency comprising (i) a base frequency which is identical to the personalized tinnitus tone (ii) a sine wave with a frequency n % above the base frequency, and (iii) a sine wave with a frequency n % below the base frequency
17—providing to the subject a tone comprising at least one sine cluster, on a set schedule, over a set period of time, thereby effecting a reduction in tinnitus symptoms.

The structure of the sine cluster is critical to the invention. In one embodiment, the sine cluster is defined as a group of three sine waves of similar amplitude comprising (i) a base frequency which is identical to the personalized tinnitus tone (ii) a sine wave with a frequency n % above the base frequency, and (iii) a sine wave with a frequency n % below the base frequency.

In another embodiment the sine cluster is defined as a group of at least three sine waves of the same or similar amplitude but varying frequency comprising (i) a base frequency which is identical to the personalized tinnitus tone (ii) a sine wave with a frequency n % above the base frequency, and (iii) a sine wave with a frequency n % below the base frequency. Therefore in this embodiment there may be more than 2 outlying waves, such as 4 or 6 outlying waves each separated by a set amount such as n % or n°.

In one preferred embodiment of the above method, n=1%, and the sine cluster is a group of three sine waves of similar amplitude comprising 9,900 Hz, 10,000 Hz, 10,100 Hz.

In other embodiments n (the difference if frequency) may equal 0.5%, 1%, 5%, 10%, 25%, 35%, or 45%; or for example between 0.5 and 5%, between 2 and 7%, between 5 and 10%, between 7 and 20%, between 10 and 30%, or between 20 and 50%.

In other embodiments the sine cluster encompasses any odd number of sine waves, for example 5, 7, 9, 11, 13, 15, 17, 19, 21, 23, 25, 27, 29 or 31 sine waves in a cluster, or more.

In a preferred embodiment, the sine cluster is played to the subject, followed by a pure tone (the personalized tinnitus tone).

In another such embodiment, the sine cluster is played to the subject for 15 minutes, followed by 45 minutes of pure tone.

Note the terms "at least" or "no more than" may equally be used to modify the stated times.

In another such embodiment, the sine cluster is played to the subject for 30 minutes, followed by 60 minutes of pure tone.

In another such embodiment, the sine cluster is played to the subject for 60 minutes, followed by 120 minutes of pure tone.

In another such embodiment, the pure tone is played to the subject for 15 minutes, followed by 45 minutes of sine cluster.

In another such embodiment, the pure tone is played to the subject for 30 minutes, followed by 60 minutes of sine cluster.

In another such embodiment, the pure tone is played to the subject for 60 minutes, followed by 120 minutes of sine cluster.

Other variations may be used for example a pure tone of between 2 mins and 120 mins and a sine cluster of between 2 mins and 120, with either the sine cluster od the pure time first and the other second. An interval period of between 1 min and 20 mins is optional.

Variations in Parameters Encompassed by the Invention

Many variations may be made in the above methods. Various ranges are set out below.

In step 1, the tone may be 9397 Hz (+/−1 Hz). Alternatively this tone may have a frequency between 1000 and 20000 Hz. In various embodiments frequency is between 8000 and 12000 Hz, 8500 and 10000 Hz or 9000 to 10000 Hz.

Exposure time may vary, and the time of exposure may be between for example 1 and 60 s, 1 and 30 s, 3 and 20 s, or 3 and 10 s.

In step 2, grading may be done on a numeric scale, for example 1-10, or simply in a qualitative way, with the subject perceiving and indicating that the tone provided is a higher or lower tone than the perceived tinnitus tone.

In step 3 the tone frequency is adjusted up or down by one octave, or alternatively by two or more octaves, or by 7, 6, 5, 4, 3, 2 or one note on a simple chromatic scale.

In step 6, the tone frequency may be adjusted up or down by 7 notes at a time, or alternatively by fewer notes such as 7, 6, 5, 4, 3, 2 or one note on a simple chromatic scale.

In step 9 the tone frequency is adjusted up or down by half notes, but alternatively may be adjusted by a smaller increment such as quarter or eighth or sixteenth tones.

10—grading the tone by the subject as either higher or lower in tone than the perceived tinnitus tone In step 15, a tone frequency ("personalized tinnitus tone frequency") may be saved in a computer memory. Various aspects of the tone may be stored, including waveform, frequency, amplitude and duration. The form of storage may be RAM such as static RAM chips, or ROM including all forms of storage including those using magnetic and optical media.

In step 16, by means of computer software, a plurality of sine clusters are created. This may be done using an algorithm programmed into and executed by a computer. A sine cluster is defined as a group of at least three sine waves of similar amplitude but varying frequency comprising (i) a base frequency and one or more additional sine waves with frequencies set a certain known degree above and below the base frequency.

In step 16 the sine cluster is defined as a group of at least three sine waves of similar amplitude but varying frequency comprising (i) a base frequency (ii) a sine wave with a frequency n % above the base frequency, and (iii) a sine wave with a frequency n % below the base frequency. In other embodiments and descriptions we can talk about the sine waves in terms of wavelength (which is inversely proportional to frequency). The sine waves may be out of phase by various set amounts, expressed in fractions or degrees, as is usual with waveform measurements. For example, each sine wave separated by a phase difference of between 1 degree and 90 degrees. Indeed any separation may be used so long as it is not 108 degrees (which would cancel out the tone) or 360 degrees (which would produce the identical tone). In one example the phase difference between sine waves may be $1/100^{th}$ of a wavelength and $1/25^{th}$ of a wavelength. In another it may be between 10° ($\chi/100$ of a radian) and 90° ($\chi/2$ radians).

In step 17 the personalized tinnitus tone frequency is then provided to the subject and forms the basis for the treatment. The personalized tinnitus tone frequency may be provided to the subject via any sort of known playback device such as a digital player such as an MP3 player, mini-disc player, CD player or analogue device such a tape player or other audio-playback device.

In early embodiments the Sine clusters target pitch values only slightly higher and slightly lower, so for a target pitch of 5,000 hz you would cluster it with something like 4,900 hz and 5,100 hz. But in further experiments we have found that better results are achieved when we target values that are octaves higher or lower than the perceived tone (doubled/halved), so on the axis of 5,000 hz we would also add waveforms of: 625 hz, 1,250 hz, 2,500 hz, 10000 hz and/or 20,000 hz. Likewise, on the 4,900 hz axis we may add waveforms of 1,225 hz, 2,450 hz, 9,800 hz and 17,600 hz, and on the 5,100 hz axis we may add waveforms of 1,275 hz, 2550 hz, and 10,200 hz. We refer to this technique as using "lattice clusters" rather than "sine clusters". In experiments this method has improved tinnitus by more than 50%.

The tone therapy is generally self-administered, and the subject will record a semi-quantitative record of the loudness of the perceived tinnitus at various times before and after treatment.

In other embodiments the tone therapy is administered by a clinician in a clinical setting such as a consulting room, clinic or hospital. In such a case the playback device may be a specialized device providing a finely tuned and accurate tone, and allowing recording of data in real time by the clinician.

A certain minimal regimen may be provided for self-administration, for example 15 minutes per day, every day. The time of administration may be set or variable. For example the subject may be asked to self-administer the tone therapy once per day, each day, in the evening just before bed-time.

Alternatively the subject may be asked to self-administer the tone therapy in the morning. It may be that one of these regimens may work better than another, so the clinician may adjust the schedule over time to determine the preferred regiment.

In other regimens the subject may be asked to self-administer the tone therapy twice or more per day, for example twice, three times, four times, 5 times or six times.

In other regimens the subject may be asked to self-administer the tone therapy hourly throughout the waking day, or at another interval such as 2-hourly or 3-hourly.

Alternatively, in other regimens the subject may be asked to self-administer the tone therapy at night, immediately prior to sleeping, and to continue the treatment through the sleeping period.

In some embodiments, the playback device may be programmed to switch off after a certain time has elapsed, for example after a set time such as after 30 mins, 1 hr, 2 hr or 3 hr.

In some embodiments, the playback device may be programmed to adjust the amplitude of the signal over a period of time, such as to reduce the volume gradually over a period of, for example, 1, 3, or 3 hours.

Embodiment 2—Treatment Using Specific Frequency of 9397 Hz

In another embodiment, the invention encompasses a method for treating tinnitus comprising subjecting a subject having tinnitus to a sound, whereby the following steps are performed:

Providing a subject suffering from tinnitus and

1—providing to the subject a tone at a frequency of 9397 Hz (+/−1.0 Hz) for between 3 and 10 seconds
2—grading the tone by the subject as either higher or lower in tone than the perceived tinnitus tone
3—adjusting the tone either up or down by one octave
4—grading the tone by the subject as either higher or lower in tone than the perceived tinnitus tone
5—repeating steps 3-4 until an approximate match is found with a resolution of no more than one octave
6—adjusting the tone up or down by 7 notes at a time
7—grading the tone by the subject as either higher or lower in tone than the perceived tinnitus tone
8—repeating steps 6-7 until an approximate match is found with a resolution of no more than 7 notes
9—adjusting the tone up or down by half notes
10—grading the tone by the subject as either higher or lower in tone than the perceived tinnitus tone
11—repeating steps 9-10 until an approximate match is found with a resolution of no more than half a note
12—adjusting the tone up or down on a continuous scale
13—grading the tone by the subject as either higher or lower in tone than the perceived tinnitus tone
14—repeating steps 12-13 until an approximate match is found such that no further adjustments in tone produce a perceived improved match ("personalized tinnitus tone")
15—saving the personalized tinnitus tone information including wavelength, frequency and amplitude, in a computer memory
16—generating by means of computer software, a plurality of sine clusters, wherein a sine cluster comprises at least three sine waves of similar amplitude but varying frequency, each sine wave separated by a phase difference of between 10 degrees and 90 degrees, and wherein at least one of the tones is the personalized tinnitus tone
17—providing to the subject a tone comprising at least one sine cluster, at least once per day for at least 15 contiguous minutes, thereby effecting a reduction in tinnitus symptoms. In a preferred embodiment, the sine cluster is played to the subject, followed by a pure tone (the personalized tinnitus tone).

In another such embodiment, the sine cluster is played to the subject for 15 minutes, followed by 45 minutes of pure tone.

The sign wave cluster may be comprised of various sets of sine waves wherein at least one of the tones is the personalized tinnitus tone. In one preferred embodiment of the above method, n=1%, and the sine cluster is a group of three sine waves of similar amplitude comprising 9,900 Hz, 10,000 Hz, 10,100 Hz.

In other embodiments the sine cluster encompasses any odd number of sine waves wherein at least one of the tones is the personalized tinnitus tone, for example 5, 7, 9, 11, 13, 15, 17, 19, 21, 23, 25, 27, 29 or 31 sine waves in a cluster, or more.

Embodiment 3—Treatment Using 9397 Hz, and a Continuous Adjustment

In another embodiment, the following steps are performed:

Providing a subject suffering from tinnitus and

1—providing to the subject a tone at 9397 Hz (+/−0.5 Hz) for between 3 and 10 seconds 2—grading the tone by the subject as either higher or lower in tone than the perceived tinnitus tone 3—adjusting the tone either up or down on a continuous scale using a rotary dial tuning control 4—grading the tone by the subject as either higher or lower in tone than the perceived tinnitus tone 5—repeating steps 3-4 until an approximate match is found such that no further adjustments in tone produce a perceived improved match ("personalized tinnitus tone")

6—saving the personalized tinnitus tone information including wavelength, frequency and amplitude, in a computer memory 7—generating by means of computer software, a plurality of sine clusters, wherein a sine cluster comprises at least three sine waves of similar amplitude but varying frequency, each sine wave separated by between 10 degrees and 90 degrees, and wherein at least one of the tones is the personalized tinnitus tone 8—providing to the subject a tone comprising at least one sine cluster, at least twice per day for at least 10 contiguous minutes, thereby effecting a reduction in tinnitus symptoms.

Embodiment 4—Treatment Using a Plurality of Triplets

In another embodiment, in step 7 the generated sine cluster comprises a plurality of triplets. The anchor triplet comprises 3 waves in which one is the personalized tinnitus tone and the other two are n % greater and lower in frequency than the personalized tinnitus tone. The other triplets are displaced from the anchor triplet by 1 octave.

Embodiment 5—Treatment Using at Least One Sine Cluster

In another embodiment, in step 8 the subject is provided with a tone comprising at least one sine cluster, at least once per day for an hour, starting at bed-time and extending into the sleep cycle of the subject.

Embodiment 6—Treatment Using a Specific Frequency

In another embodiment, in step 1 the subject is provided with a tone of exactly 9397.272573 hz.

Embodiment 7—Treatment Using a Specific Frequency and Duration

In another embodiment, in step 1 the subject is provided with a tone of exactly 9397.272573 hz for 3-10 seconds.

Embodiment 8—Treatment Providing the Tone Via Headphones

In another embodiment, the tone is provided to the subject via headphones.

Embodiment 9—Treatment Providing the Tone Via Bone-Conduction

In another embodiment, the tone is provided to the subject via bone-conduction headphones.

Embodiment 10—Treatment Providing the Tone Via SoundBeamer™

In another embodiment, the tone is provided to the subject via SoundBeamer technology from Noveto Systems, which uses a 3-D sensing module and locates and tracks the ear position sending audio via ultrasonic waves to create sound pockets by the user's ears. Sound can be heard in stereo or a spatial 3-D mode that creates 360 degree sound around the listener. This technology is encompassed in U.S. Ser. No. 14/443,019 which is hereby incorporated by reference.

Embodiment 11—Treatment Providing a Specific Volume Range

In another embodiment, the tone is provided at a volume of between 60 db and 100 db.

Embodiment 12—Treatment Providing a Specific Volume

In another embodiment, the tone is provided at a volume of about 80 db.

Embodiment 13—Treatment Using Noise-Cancelling Headphones

In another embodiment, the tone is provided by noise-cancelling over-ear headphones. These may be active noise-cancellation (ANC) devices that work by using microphones to pick up low-frequency noise and neutralize it before it reaches the ear. A generated sound that is phase-inverted by 180° cancels out the unwanted sounds.

Embodiment 14—Treatment Using Various Waveforms in an ACR Cluster

Figure 1:
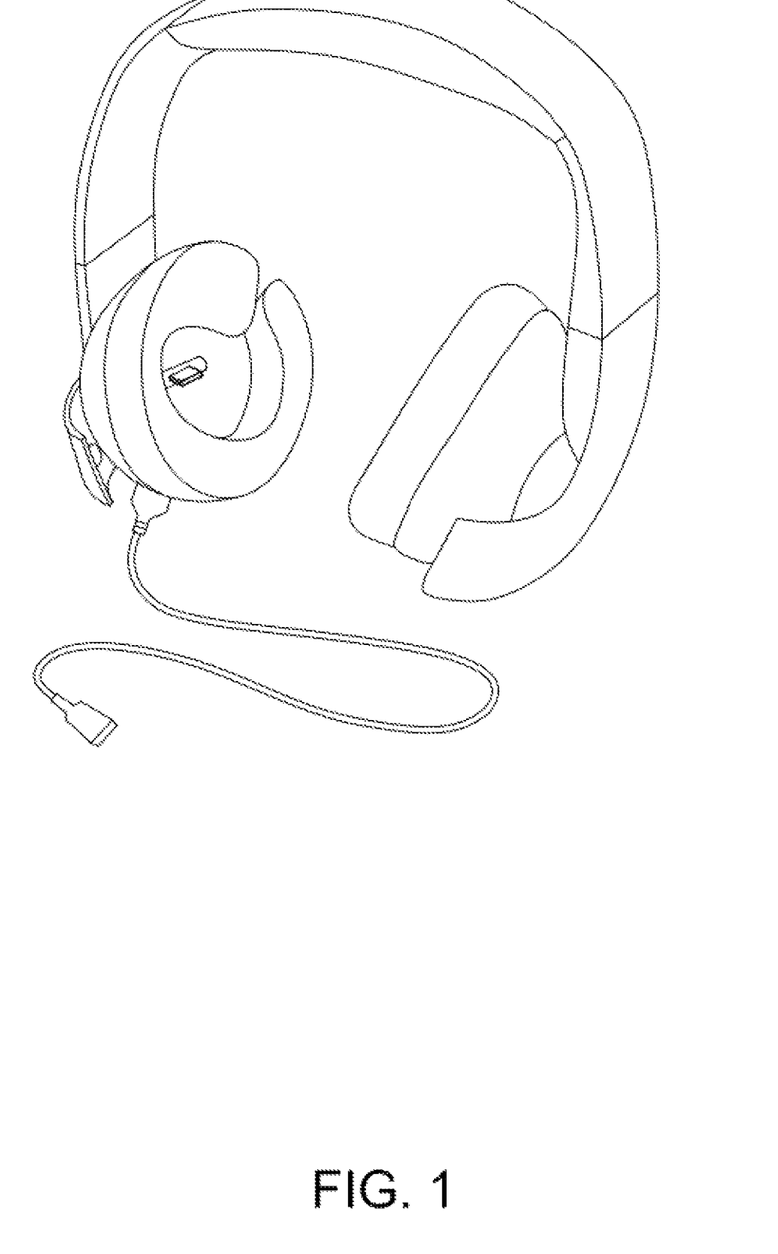
FIG. 1. Docking Bay Headphones (Prior Art)
FIG. 2. Undocked Bone Conduction Headphones w/Lithium Ion Battery (Prior Art)
FIG. 3. Docked Bone Conduction Headphones (Prior Art)
FIG. 4. Various waveforms used: sine, square, ramp, sawtooth and triangular.
Figure 2:
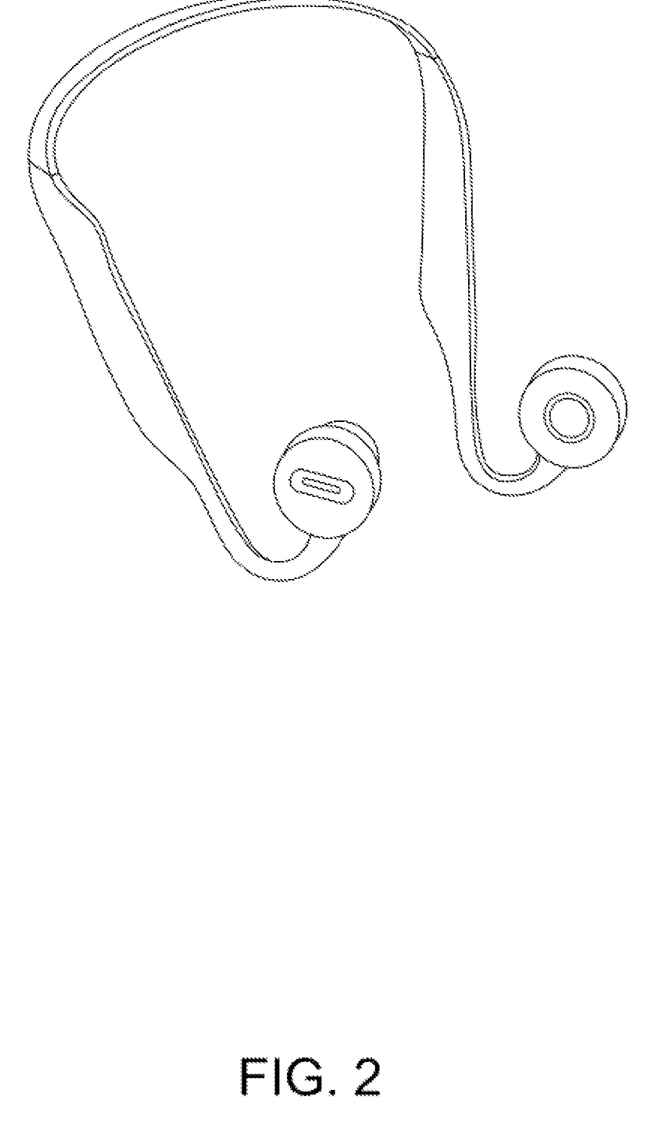
Figure 3:
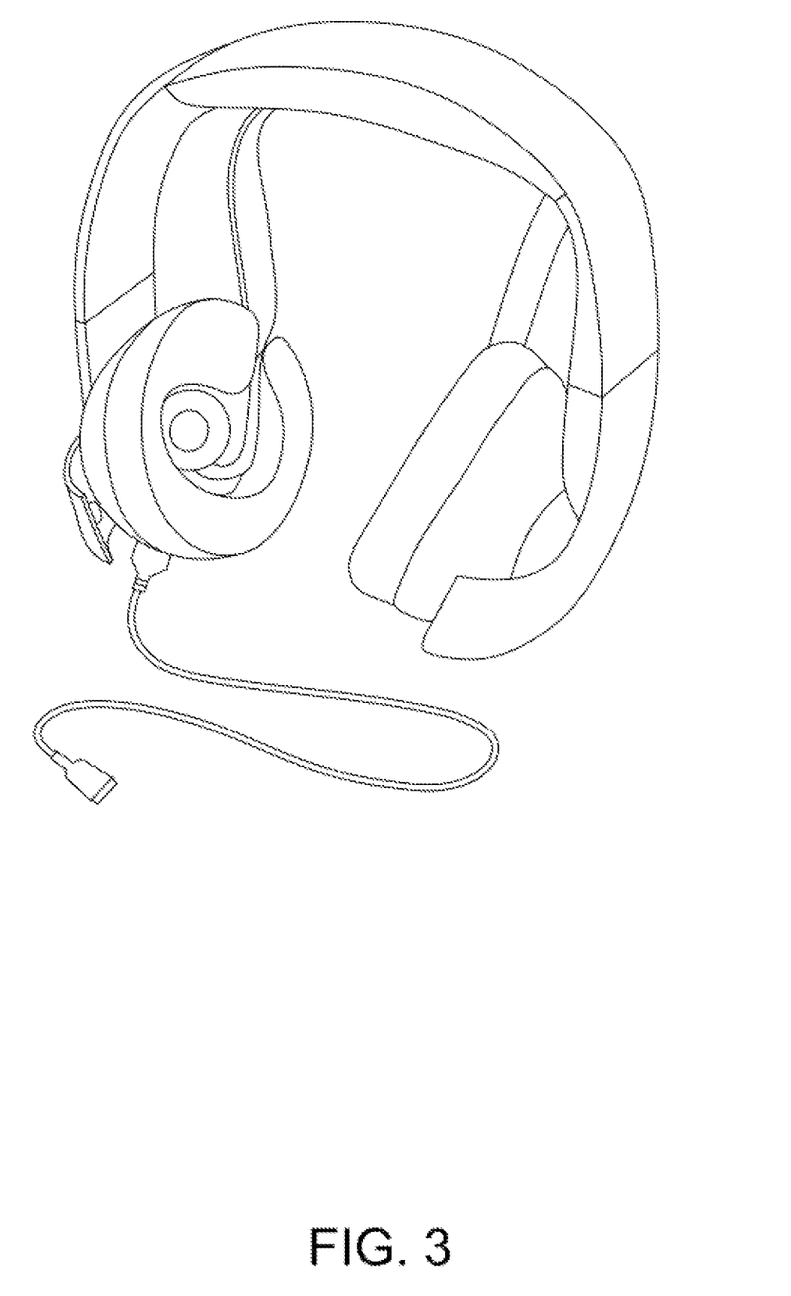
Figure 4:
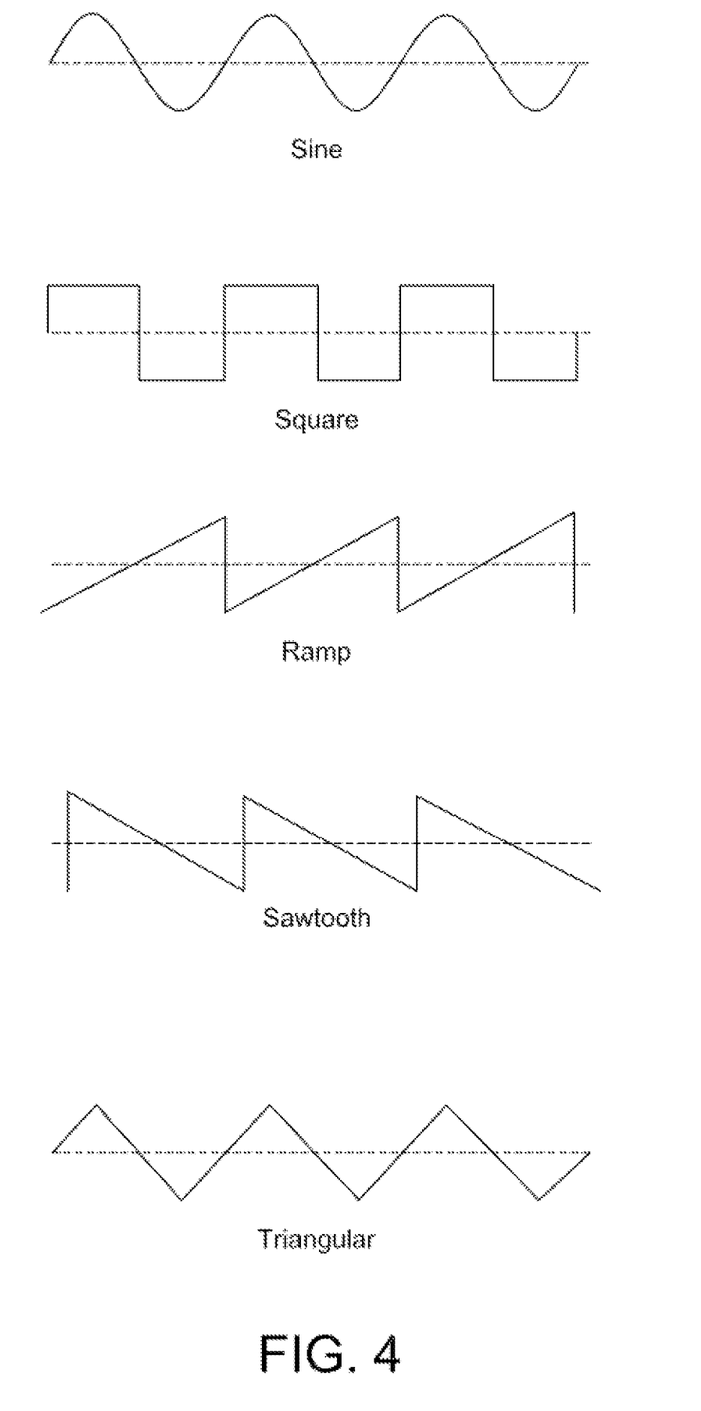
Figure 5:
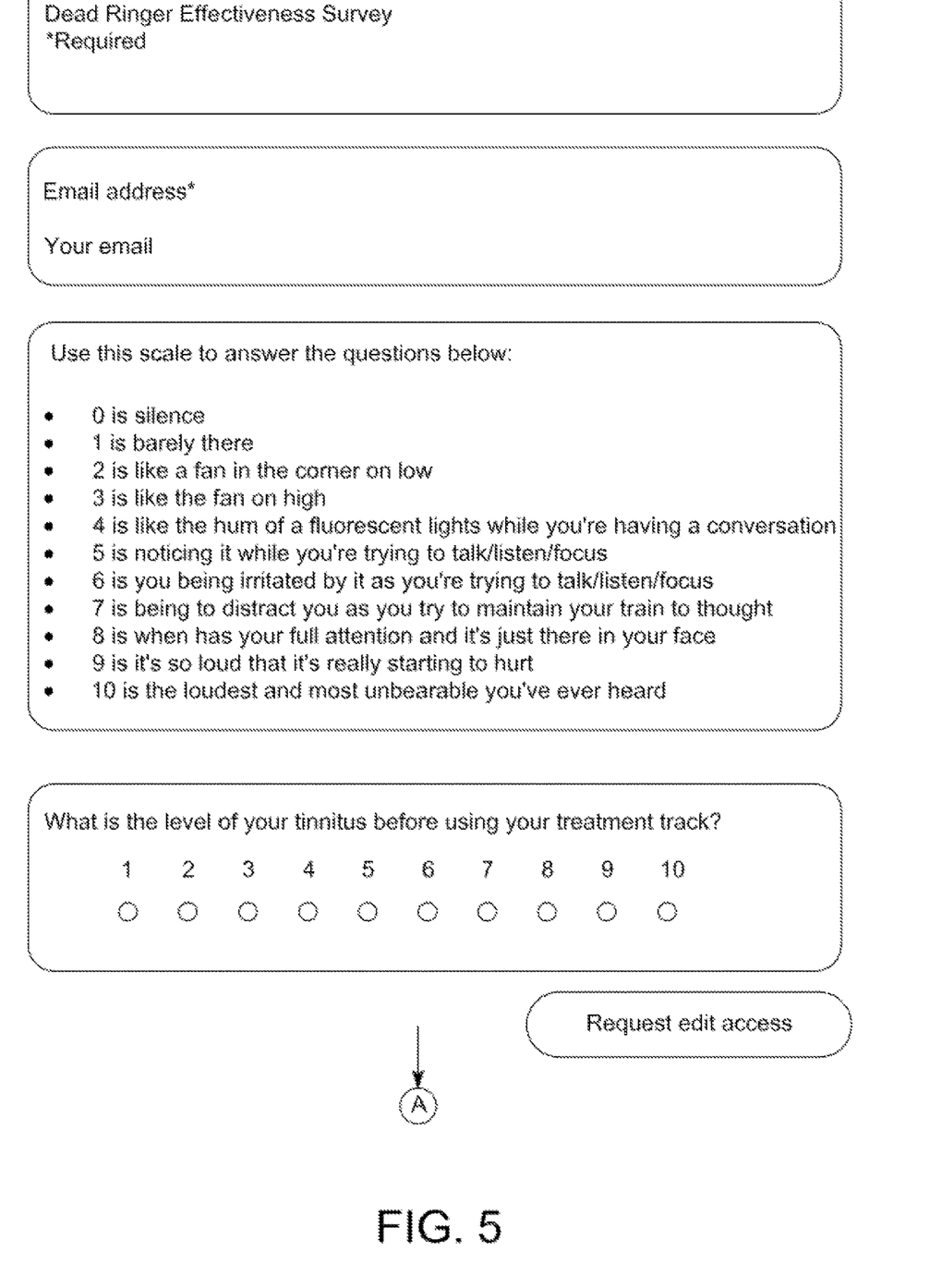
FIG. 5. Shows a typical effectiveness survey questionnaire used with the method of the invention.

The majority of standard embodiments discussed herein employ standard sine waveforms (such as Embodiment 1, subsect. 16). However, the applicant has investigated other waveforms. Specifically the inventor has experimented with the following waveforms: sine, square, ramp, saw-tooth and triangular. See FIG. 4.

An Acoustic Coordinated Reset (ACR) Cluster may be used instead of the typical sine cluster. The ACR Cluster can be defined as any combination of at least three of the five periodic waveforms (sine, square, triangle, ramp, and saw-tooth) such that the "root pitch" R is encapsulated by the "ceiling pitch" C and the "floor pitch" F with up to 30 "insulating pairs" at evenly spaced intervals above and below the root frequency. A root pitch is derived from the self-reporting of a perceived "phantom" tone by a patient with tinnitus, and the ACR Cluster is used for the sole purpose of Acoustic Coordinated Reset Neuromodulation tinnitus treatment.

In one example, a simple ACR Cluster might be composed of three sine waves with a root frequency of 5,000 Hz, a floor of 4,800 Hz, and a ceiling of 5,200 Hz.

In another example, the values of the root, ceiling, and floor frequencies might be 5,000 Hz, 4,800 Hz, and 5,200 Hz respectively, but the root might be a square wave, the floor might be a sine wave, and the ceiling might be a triangle wave.

In another example, the waveforms might all be sine waves, but in addition to the root of 5,000 Hz, the floor of 4,800 Hz, and the ceiling of 5,200 Hz, there might also be two "insulating pairs" of waveforms, with "pair 1" being 4,850 Hz and 5,150 Hz, and "pair two" being 4,900 Hz and 5,100 Hz.

In an additional example, the root might be a sine wave of 5,000 Hz, the ceiling and floor might be square waves or 4,800 Hz and 5,200 Hz with one insulating pair of saw-tooth waves at 4,900 Hz and 5,100 Hz.

Specifically the ACR embodiment may encompass:

A method for treating tinnitus comprising subjecting a subject having tinnitus to a sound, whereby the following steps are performed: providing a subject suffering from tinnitus and (i) providing to the subject a tone with a frequency between 10 Hz and 20000 Hz,
(ii) subjective grading of the tone by the subject as being either higher or lower in tone than the perceived tinnitus tone,
(iii) adjusting the tone either up or down by one octave,
(iv) subjective grading of the tone by the subject as being either higher or lower in tone than the perceived tinnitus tone,
(v) repeating steps iii-iv until an approximate match is found with a resolution of no more than one octave,
(vi) adjusting the tone up or down by 7 notes at a time,
(vii) subjective grading of the tone by the subject as being either higher or lower in tone than the perceived tinnitus tone,
(viii) repeating steps vi-vii until an approximate match is found with a resolution of no more than 7 notes,
(ix) adjusting the tone up or down by half notes (e.g.: C, C#, D, D#, E, E#),
(x) subjective grading of the tone by the subject as being either higher or lower in tone than the perceived tinnitus tone,
(xi)—repeating steps ix-x until an approximate match is found with a resolution of no more than half a note,
(xii) adjusting the tone up or down on a continuous scale,
(xiii) subjective grading of the tone by the subject as being either higher or lower in tone than the perceived tinnitus tone,
(xiv) repeating steps xii-xiii until an approximate match is found such that no further adjustments in tone produce a perceived improved match ("personalized tinnitus tone"),
(xv) storing the personalized tinnitus tone information including wavelength, frequency and amplitude, in a memory,
(xvi) generating by means of computer software, a plurality of waveform clusters, wherein a waveform cluster is defined as a group of three waves of similar amplitude but varying frequency comprising (i) a base frequency which is identical to the personalized tinnitus tone (ii) a wave with a frequency n % above the base frequency, and (iii) a wave with a frequency n % below the base frequency,
(xvii) providing to the subject a tone, on a set schedule, over a set period of time, thereby effecting a reduction in tinnitus symptoms.
wherein, in xvi, in the plurality of waveform clusters comprises an Acoustic Coordinated Reset (ACR) Cluster defined as any combination of at least three of the five periodic waveforms (sine, square, triangle, ramp, and saw-tooth) such that the "root pitch" (R) is bounded by the "ceiling pitch" (C) above and the "floor pitch" (F) below, and wherein up to 30 additional pairs of waveforms are provided at evenly spaced intervals above and below the root frequency, and wherein the root pitch is derived from the self-reported tinnitus tone.

Embodiment 14—A Preferred Embodiment as Used Experimentally (i) A subject suffering from tinnitus is identified.
(ii) The subject completes a questionnaire that includes the following questions:
(a) list any medications you have taken in the last 72 hours.
(b) list any medications you have taken in the last 24 hours. e.g. caffeine, nicotine, albuterol.
(c) list any depressants/inhibitors you have taken in the last 24 hours e.g. alcohol, marijuana etc.

The above information is recorded.
1. Subject is told that:
0 is silence
1 is just barely there
2 is like a fan in the corner on low
3 is like the fan on high
4 is like the hum of a fluorescent lights while you're having a conversation
5 is noticing it while you're trying to talk/listen/focus
6 is you being irritated by it as you're trying to talk/listen/focus
7 is beginning to distract you as you try to maintain your train of thought
8 is when has your full attention and it's just there in your face
9 is it's so loud that it's really starting to hurt
10 is the loudest and most unbearable they ever heard
2. Technician collects a full biopsychosocial background interview for subject's tinnitus: work environment history, pharmaceutical regimen, loud flashbulb memories, known incidents of auditory pathway trauma.
3. The patient is then asked to rate their tinnitus as it was during the time they described it.
4. The quality/waveform, approximate volume in dB, and pitch in Hz
5. The tinnitus technician now shares their screen with the patient and attempts to create the most accurate representation of the phantom intrusion occurring in their auditory cortex. If, after working with the tinnitus technician to emulate the intrusion, the replica can be qualified as a single frequency and waveform, the tinnitus will be classified as a simple intrusion, or Type 1 Tinnitus. Alternatively, if the replica presents with multiple layers, pitches, or noise patterns, the complex intrusion will be classified as Type 2 Tinnitus, the tinnitus technician will exit this protocol and open the Type 2 Tinnitus Manual.
6. Type 1 Tinnitus patients will be administered the Chromatic Ballpark Algorithm until they decide on a replica.
7. The replica will be processed by an audio technician into a rendered treatment file, put onto a microSD card, and given to the patient.
8. The tinnitus technician will guide the patient through the attentive association method using the replica.
9. The tinnitus technician will then finish out the patient's record
10. The tinnitus technician will counsel with the patient to create a detailed treatment plan catered to realistic expectations.

11. The Treatment Package will consist of data collection instructions, the treatment file on a microSD card loaded into standardized bluetooth headphones which are then mailed to the patient.

12. The tinnitus technician will check in with the patient every week for a total of 3 months to collect data, recalibrate a new treatment file if the patient reports a significant change in their phantom intrusion (e.g. pitch, localization, waveform texture, etc.).

A preferred treatment regimen is as follows:
(i) The individualized sine cluster is determined as described herein.
(ii) This sine cluster is played to the subject for 15 minutes, followed by 45 minutes of pure tone.
(iii) The same sine cluster is played for 30 minutes followed by 60 minutes of pure tone.
(iv) The same sine cluster is played for 60 minutes followed by two hours of pure tone
(v) The order is reversed, so that pure tone is played first for 45 and then the sine cluster is played for 15 mins.
(vi) The pure tone is played for 60 minutes followed by 30 minutes of sine cluster.
(vii) The pure tone is played for 2 hours of pure tone, followed by 60 minutes of sine cluster.

Experimentally, results are measured and recorded for each cohort after one session, and after one week of doing one session daily, and then finally after one month of doing a treatment session 3-5 times a week.

The Associative Method

Subject is instructed to:
1. Listen and focus on only their phantom intrusion for 60 seconds
2. Listen to their replica for 60 seconds while attempting to associate the phantom intrusion with the replica.
3. Instruct the subject take a break for 5 minutes and engage in conversation with the tinnitus technician without paying any attention to the tinnitus.
Repeat steps 1-3 twice.

Clinical End-Points and Goals

The invention provides treatment for tinnitus, and various clinical goals and end-points provide important claim limitations. The treatment can provide a reduction in perceived tinnitus by 50-100%.

Tinnitus may be measured by various means, and the invention encompasses any such methods, including, for example:

Speech recognition test, sometimes called speech audiometry.

Pure tone audiogram, a subjective test that measures the patient's hearing across multiple frequencies.

Tympanogram, an objective test that measures the functioning of the middle ear, specifically the mobility of the tympanic membrane.

Acoustic reflex testing, an objective test that measures the contraction of the middle ear muscles in response to sounds.

Otoacoustic emission testing, the use of very sensitive microphones to objectively measure the movement of hair cells within the middle ear.

Tinnitus sound matching, which uses the presentation of common tinnitus sounds back to patients, to help them identify their specific perception of tinnitus.

Minimum masking level, which determines the volume at which an external narrowband noise masks (or covers) the perception of tinnitus.

Loudness discomfort level, which determines the volume at which external sound becomes uncomfortable or painful for a tinnitus patient.

Other questionnaire-based measurements may be used, including: Tinnitus Handicap Inventory, Tinnitus Reaction Questionnaire, Tinnitus Functional Index, Tinnitus Primary Functions Questionnaire, Tinnitus Handicap Questionnaire.

See "Measurement of Tinnitus" by James Henry; Otology & Neurotology: September 2016—Volume 37—Issue 8—p e276-e285—incorporated by reference herewith.

Any of these methods can be used to determine a reduction in tinnitus symptoms by 50-100%. Reduction may be from, for example 5%-50%, 10%-75%, 30%-60%, 5%-95%, or 50% to 100%. Or methods may result in at least 5%, 10%, 20%, 40%, 50% or at least 60% reduction.

Unexpectedly Superior Results

One of the most important aspects of the present application, and the impetus to commercialize the Dead Ringer system, is that upon clinical experimentation, the inventor has repeatedly demonstrated UNEXPECTEDLY SUPERIOR RESULTS, as follows: In addition to the consistent 50-100% reduction results I have achieved with my father, Case Study Owen Amman has used a 1-hour ACR cluster track designed by Derek Holley roughly 3 times per week for the last 6 weeks, and it has taken his tinnitus from a 4 to a 0 each time for several hours following each instance: a 100% reduction.

Experimental Methods

The method includes an initial assessment and questionnaire, followed by a treatment regimen.

A preferred experimental method is set out as follows:
(i) A subject suffering from tinnitus is identified.
(ii) The subject completes a questionnaire that includes the following questions:
  (a) list any medications you have taken in the last 72 hours.
  (b) list any medications you have taken in the last 24 hours. e.g. caffeine, nicotine, albuterol.
  (c) list any depressants/inhibitors you have taken in the last 24 hours e.g. alcohol, marijuana etc.
The above information is recorded.
(ii) The subject provides a subjective assessment of their tinnitus on a scale of 1-10 for amplitude and optionally approximates the note on a traditional diatonic scale.

A preferred treatment regimen is as follows:
(i) The individualized sine cluster is determined as described herein.
(ii) This sine cluster is played to the subject for 15 minutes, followed by 45 minutes of pure tone.
(iii) The same sine cluster is played for 30 minutes followed by 60 minutes of pure tone.
(iv) The same sine cluster is played for 60 minutes followed by two hours of pure tone
(v) The order is reversed, so that pure tone is played first for 45 and then the sine cluster is played for 15 mins.
(vi) The pure tone is played for 60 minutes followed by 30 minutes of sine cluster.
(vii) The pure tone is played for 2 hours of pure tone, followed 60 minutes of sine cluster.

Experimentally, results are measured and recorded for each cohort after one session, and after one week of doing one session daily, and then finally after one month of doing a treatment session 3-5 times a week.

Below are a number of records from experiments carried out by the inventor.

Experiment 1

Aim: To determine subject's upper hearing limit.

Assumptions: Normal level of person-to-person conversation is ~60-70 db

The frequency range of human hearing is ~10 to (up to) ~20000 Hz.

Method: A tone of 150 Hz (low-normal human voice) is provided to the subject through headphones at ~44 db. The pitch of the tone is increased and/or decreased by 1000 Hz starting from 4000 Hz until it is too high, then down to 500, 250, 125, 75, 50, 25 Hz. The amplitude (measured in dB) is increased and/or decreased by 10, 5, 2, 1 dB. The wave shape of the tone is Sine wave. Though in other embodiments it can be a saw, triangle, or a square-wave.

Results: At or just above the subject's upper audible frequency limit, subject only heard a "click" of the tone stopping for 13600 Hz, but heard the tone at same dB level for 13500, therefore upper range=13500 dB. 13500 dB is the same approximate point subject placed the tinnitus tone he heard when tested a week previously.

Discussion: The experimenter reasons that whatever "type" of tinnitus subject has is equivalent to the constant perception of a tone at the upper limit of his age-decayed audition. This tone becomes noticeable to the subject at roughly 66 dB when the volume is slowly increased. Approximate tinnitus tone therefore is 13500 hZ at 66 dB. The experimenter reasons that assuming this tone is constantly playing in the background of perception, it would be hard to notice when a loud tone of that same frequency stopped if we were to slowly turn the dial down. Following that logic, we play tones increasing in loudness and then suddenly cut them off after 10 seconds each of dB levels at: 66, 71, 76, 81, 86, 91, 96.

Experiment 2

Aim: The aim of this experiment was to create an endless tone at the approximate tinnitus frequency perceived by the subject, and play it through the headphones. We let the subject control the dial to adjust the tone.

Method: A tone was generated and played to the subject through headphones controlled by a hand-turned dial that plugs in to the headphones, which shuts itself off when tapped on top. The subject was interviewed to discuss how the subject sometimes hears "lower tones". The experimenter had prepared both a sine wave and a sawtooth wave (as a sawtooth wave is a more naturally-occurring sort of sound vs a sine wave's purely digital existence), each at 13.5 kHZ. After beginning by having the subject gradually turn each waveform up and down with a physical dial, the subject had problems detecting the presence of the "real" sine tone (playing through the headphones) until he turned the volume up to such a high amplitude that the purity of the sine wave began to distort/degrade. This distortion—with noticeable overtones and undertones until turned back down—strongly resembled a square wave in nature, and was better suited to the beginning task of distinguishing between real vs hallucinated sound. The ability to turn up the volume using a more robust sound that included both harmonics and undertones gave the subject a distinct feeling of control over both signals. After repeating this process for ~15 minutes, the subject removed his headphones and reported his tinnitus symptoms as quieter by approximately 30%.

Result: Psychological control over a perceived signal appears to be an important element to the syndrome of tinnitus.

Conclusion: Treatment is effective with room for improvement.

Experiment 3

Aim: To determine effectiveness using sine wave at 12500 hz.

Method: Subject was exposed to a sine wave of 12500 hz projected through a speaker. It was then adjusted to 12250 hz. Suddenly the subject reported that his tinnitus as gone completely. Disappointingly, we found that the effect only took place in the experimental room of roughly 20 square feet with a sound shielding curtain in the middle. We then replaced the speaker with headphones (that can play a pure sine wave on a high range without undertones). The subject initially reported hearing the tone (with the volume at 100%). After reducing the volume to about 35%, the subject reported hearing his tinnitus again. Raising the volume to 68%, the subject once again found the tone to be cancelling the perceived tinnitus tone completely.

The subject was then asked to adjust the volume coming through the headphones, and he reported that both 40-60% volume and 100% volume seemed to have the same cancelling effect. This means that there is a minimum amplitude necessary to achieve cancellation when possible, and thus this minimal exposure should be considered during treatment as a factor—whether or not to expose a subject to higher than necessary amplification may have both short and long-term effects that are in need of more rigorous testing.

Result: After determining the efficacy of the sine wave selected, the subject removed the headphones and let the effect settle in. He reported first a decrease in volume, then a new and lower frequency of tone to the tinnitus. Using approximate chromatic pitch-matching, he put the original tone at an E (the actual tone was 13. kHZ, which is closer to a flat A #), and the new tone lowered approximately at a high G or G # or, one half 12-step chromatic octave. This new, lowered tone throbs with his heartbeat and changes in timbre with jaw movements as reported with the original tone in Session 1.

CONCLUSIONS

Through experimentation detailed herein, the principle investigators have developed a number of possible hypotheses related to tinnitus and the treatment thereof.

Hypothesis #1: Tinnitus is too broadly used as a name for multiple different disorders, all of which are frequently dismissed by medical personnel as "noise where silence should be perceived." In cases where the nature of the cause is brain-based in nature, I propose that activation of the entire auditory pathway using a replica of a patient's tinnitus will cause an otherwise arbitrary brain-based hallucination to self-correct in both short-term relief and over time if the stimulus is used frequently enough. The known neuroplasticity of brains up until their absolute inability to continue cell division by shortened telomerase implies that there ought to be a solution to any brain-based form of tinnitus given sufficient research into the input/outcome dynamics.

Hypothesis #2:

1. a bundle of pitch-dedicated neurons are constantly firing in the auditory cortex as if in constant seizure activity, and thereby adding more stress to those dedicated neurons, which eventually 'burn out' into a hyperpolarized state of inactivity. If this "burnout" hypothesis is correct, it means that the temporary reduction of symptoms is the best possible goal (which will likely be true for some patients and not others). However, research has shown that this reduction of symptoms can have a long-term effect, which suggests that the auditory cortex or another mediating part of cerebral anatomy may adjust around this lessened symptom over time.

Hypothesis #3: There is a way for neurons to encode a sine wave as if it were actually occurring in some electrophysiological way. If this is the case, then phase cancellation could function within the brain between the internal and external stimuli. Without proper measurement tools and a full lab of qualified personnel at my disposal I cannot comment any further.

Hypothesis #4: Auditory confusion comes from the fact that audition in humans is supposed to give an approximate location for each sound observed. Alternating quickly from side to side with a sine wave (not heard in nature) with a rapid panning (also not natural) confused the cortex to the extent that it was effectively paralyzed for several minutes after exposure. The tone, upon returning, manifested at ~8800 hz at first, then jumped to 11000 hz before eventually returning to the original tone of 12250.

The invention claimed is:

1. A method for treating tinnitus, said method comprising identifying a subject having tinnitus, said subject perceiving a perceived tinnitus tone, and performing the following steps:
   (i) providing to the subject a tone between 10 Hz and 20000 Hz,
   (ii) indicating, by the subject, said tone as being either higher or lower in tone than the perceived tinnitus tone,
   (iii) adjusting the tone either up down by one octave,
   (iv) indicating, by the subject, said tone as being higher or lower in done than the perceived tinnitus tone,
   (v) repeating steps iii-iv until a match is found with a resolution of no more than one octave,
   (vi) adjusting the tone up or down by 7 notes at a time,
   (vii) indicating, by the subject, said tone as being either higher or lower in tone than the perceived tinnitus tone,
   (viii) repeating steps vi-vii until a match is found with a resolution of no more than 7 notes,
   (ix) adjusting the tone up or down by half notes,
   (x) indicating, by the subject, said tone as being either higher or lower in tone than the perceived tinnitus tone,
   (xi) repeating steps ix-x until a match is found with a resolution of no more than half a note,
   (xii) adjusting the tone up or down on a continuous scale,
   (xiii) indicating, by the subject, said tone as being either higher or lower in done than the perceived tinnitus tone,
   (xiv) repeating steps xii-xiii until a match is found such that no further adjustments in tone produce a perceived improved match, wherein the match is found such that no further adjustments in tone produce a perceived improved match is a personalized tinnitus tone,
   (xv) storing information of the personalized tinnitus tone, said information including wavelength, frequency, and amplitude, in a memory,
   (xvi) generating, by means of computer software, a plurality of waveforms forming a waveform cluster, wherein the waveform cluster is defined as a group of at least three waves of a same amplitude but varying frequency comprising (i) a base frequency which is identical to the personalized tinnitus tone, (ii) a wave with a frequency n % above the base frequency, and (iii) a wave with a frequency n % below the base frequency, wherein n is a number between 0.5 and 45, and
   (xvii) providing to the subject a tone comprising the waveform cluster in (xvi), on a set schedule, over a set period of time, thereby effecting a reduction in tinnitus symptoms.

2. The method of claim 1 wherein the tone provided in step (i) is between 7000 Hz and 12000 Hz.

3. The method of claim 1 wherein the tone provided in step (i) is between 9000 Hz and 10000 Hz.

4. The method of claim 1 wherein the tone provided in step (i) is provided for between 1 and 10 seconds.

5. The method of claim 1 wherein, in step (xvi), in the waveform luster, all waveforms are sine waveforms.

6. The method of claim 1 wherein, in step (xvi), in the plurality of waveforms, all waveforms are square waveforms.

7. The method of claim 1 wherein, in step (xvi), in the waveform cluster, all waveforms are saw-tooth waveforms.

8. The method of claim 1 wherein, in step (xvi), in the waveform cluster, all waveforms are ramp waveforms.

9. The method of claim 1 wherein, in step (xvi), in the waveform cluster, all waveforms are triangular waveforms.

10. The method of claim 1 wherein, in step (xvi), in the waveform cluster, each of the waveforms in the cluster are selected from a group consisting of: sine, square, ramp, saw-tooth and triangular waveforms.

11. The method of claim 1 wherein, in (xvi), the waveform cluster comprises at least three of five periodic waveforms, said periodic waveforms being sine, square, triangle, ramp, or saw-tooth waveforms.

12. The method of claim 11 wherein a root pitch frequency (R)=3000-7000 Hz, a floor pitch frequency (F)=1000-5000 Hz, and a ceiling pitch frequency (C)=5000-20000 Hz.

13. The method of claim 12 wherein the frequency of R=4000-6000 Hz, F=3000-4000 Hz, and C=6000-7000 Hz.

14. The method of claim 1 wherein the subject is provided with the waveform cluster of step (xvi) for 15-60 minutes, followed by 45-180 minutes of the perceived tinnitus tone.

15. The method of claim 14 wherein the subject is provided with the waveform cluster of step (xvi) for 15-30 minutes, followed by 45-60 minutes of the perceived tinnitus tone.

16. The method of claim 14 wherein the subject is subjected to the method 3-5 times a week.

17. The method of claim 1 wherein the tone provided in step (i) is between 7000 Hz and 12000 Hz, and wherein in step (xvi), n is between 0.5 and 10, and wherein in step (xvi), in the waveform cluster, all waveforms are sine waveforms, and wherein the subject is provided with the waveform cluster of step (xvi) for 15-30 minutes, followed by 45-60 minutes of the perceived tinnitus tone, and wherein the treatment method is provided 3-5 times a week.

18. The method of claim 17 wherein the waveform cluster comprises at least 5 separate sine waves of a same amplitude but varying frequency.

* * * * *